United States Patent [19]

Krumeich

[11] Patent Number: 5,110,590
[45] Date of Patent: * May 5, 1992

[54] USE OF A SOLUTION OF ALPHA-CHYMOTRYPSIN

[76] Inventor: Jorg H. Krumeich, Propst-Hellmich-Promenade 28, D4630 Bochum 6, Fed. Rep. of Germany

[*] Notice: The portion of the term of this patent subsequent to Sep. 22, 2004 has been disclaimed.

[21] Appl. No.: 475,883

[22] Filed: Feb. 6, 1990

Related U.S. Application Data

[63] Continuation-in-part of Ser. No. 930,769, Nov. 14, 1986, abandoned, which is a continuation-in-part of Ser. No. 826,337, Feb. 5, 1986, Pat. No. 4,695,458.

[51] Int. Cl.$^5$ .................. A61K 37/547; A61K 37/553
[52] U.S. Cl. ................................... 424/94.64; 514/912
[58] Field of Search ................ 424/94, 94.64; 514/912

[56] References Cited

U.S. PATENT DOCUMENTS 4,695,458  9/1987  Krumeich ............................ 424/94

OTHER PUBLICATIONS

Lifecore Biomedical—Patents and Copyrights (Abstract).
Sodium Hyaluronate in Anterior Segment Surgery: A Review and a New Use in Extracapsular Surgery (Abstract).
Vitrax Sodium Hyaluronate in Anterior Segment Surgery A Review and Clinical Study Summary (Abstract).
Aq. Solns. of Carboxymethylcellulose or Salts—Used as Ophthalmic Viscoelastic Surgical Material in Anterior Chamber of Eye (Abstract).
Methycellulose for Endothelial Cell Protection (Abstract).
Viscoelastic Soln. Used in Ophthalmic Operations—Comprising HPMC Dissolved in $H_2O$ in Spec. Conc. for Injection into Lens (Abstract).

Primary Examiner—Frederick E. Waddell
Assistant Examiner—Diane Gardner
Attorney, Agent, or Firm—Clifford A. Poff

[57] ABSTRACT

Preparation and use of a composition of alpha-chymotrypsin in either a physiologically suitable solution or suspension medium, in a dilution of 1:10,000 to 1:30,000, corresponding to a ratio of amounts of 1 milligram of alpha-chymotrypsin to 10 to 30 milliliters of the solution medium, or in a dispersion, by volume, of preferably 1:15,000 to 1:20,000 of the alpha-chymotrypsin to the suspension medium, for the treatment and cleaning of the posterior lens capsule left behind in an extracapsular cataract operation. The composition, in its final application solution or dispersion form contains an amount of a viscoelastic substance adapted for intraocular or intraorbital surgical operations and suitable for combatting or preventing unwanted further dilution of the alpha-chymotrypsin, regardless of the amount of fluids either present or subsequently collected in the eye during the posterior lens cleaning operation.

31 Claims, No Drawings

USE OF A SOLUTION OF ALPHA-CHYMOTRYPSIN

The present invention is a continuation-in-part of U.S. patent application Ser. No. 930,769, filed Nov. 14, 1986, now abandoned, which is a continuation-in-part of U.S. patent application Ser. No. 826,337, filed Feb. 5, 1986 and granted U.S. Pat. No. 4,695,458.

BACKGROUND OF THE INVENTION

1. Field of the Invention

This invention relates to compositions of matter useful in performing extracapsular cataract operations and to a method of performing such operations with the use of such compositions. More particularly, the invention relates to the use of a solution of alpha-chymotrypsin in the area of operative treatment of grey cataract.

2. Description of the Prior Art

Grey cataract is an ailment of the eye in which there develops a darkening or clouding of the lens and a decrease of vision produced thereby. By a so-called intracapsular operation, the darkened or clouded lens, which is located in a capsule, is removed by extraction as a whole together with the capsule.

By another method, a so-called extracapsular operation, which is presently widely used, the darkened or clouded lens is likewise removed, but the posterior capsule is left behind. In performing an extracapsular operation, the anterior capsule of the lens is removed and then the main part of the lens and the intracapsular posterior rind coating are drawn away with the aid of a flushing process with simultaneous irrigation. There also exists the possibility of using an ultrasonic sound apparatus for the destruction of the main body of the lens and its removal by aspiration. In most cases, there is practiced in such operations the subsequent implantation of a clear typically glass-bodied posterior chamber lens which replaces the removed darkened or clouded lens. A prerequisite for this is that the posterior capsule be exposed by the operation and that the capsule be completely clear so that optimum physiological (optical) properties including complete light transmission are restored, hence indicating success of the operation. It is known to mechanically polish the posterior capsule before the implantation of the posterior chamber lens. However, despite careful polishing, there frequently develops a so-called capsule fibrosity; this concerns a thickening of the capsule because of very fine particles which cannot be seen microscopically but which form a thickened film on the capsule during the operation.

Alpha-chymotrypsin is a substance that in its cleanest, crystallized, dialyzed and stabilized form is commercially available. Its molecular weight is 22,500; its isoelectric point lies between a pH value of 5 to 4, with the effective maximum being at 8.1 to 8.6.

The use of alpha-chymotrypsin is known for the practice of intracapsular operations. In such operations, it is used in a dilution of 1:5,000 to about 1:10,000 and it serves for enzymatic zonulolysis, that is, the dissolution of the zonule fibers that hold the lens in tension. It was therefore surprising to establish, and not foreseeable, that the same substance could be used in a dilution of 1:10,000 to 1:30,000 whereby the fibers are not dissolved and the solution can be used for the cleaning of the posterior capsule.

During such cleaning, it has been discovered that, in some circumstances, there exists a problem in that liquid present in the eye or liquid forming or collecting in the capsule may undesirably further dilute the alpha-chymotrypsin solution. Accordingly, there has been a need for a further modification or improvement in accordance with which the composition of the alpha-chymotrypsin solution is suitably modified to overcome this problem. There is a looseleaf reference work, periodically updated and available to U.S. pharmacists, called "Facts and Comparisons", published by the Lippincott firm of St. Louis, Missouri, and it contains information that sodium hyaluronate is known to be naturally present in the aqueous humour and vitreous humour of the eye, and that sodium hyaluronate is known as a specific material which is useful in extracapsular eye surgery. There is not to be derived from this information, however, any particular suggestion of its role in the preferred embodiment of the present invention.

SUMMARY OF THE INVENTION

A preparation and use of a composition of alpha-chymotrypsin in either a physiologically suitable solution or suspension medium in a dilution of 1:10,000 to 1:30,000, corresponding to a ratio of amounts of 1 milligram of alpha-chymotrypsin to 10 to 30 milliliters of the solution medium, or in a dispersion, by volume, of preferably 1:15,000 to 1:20,000 of the alpha-chymotrypsin to the suspension medium, for the treatment and cleaning of the posterior lens capsule left behind in an extracapsular cataract operation. The composition, in its final application solution or dispersion form contains an amount of a viscoelastic substance adapted for intraocular or intraorbital surgical operations and suitable for preventing unwanted further dilution of the alpha-chymotrypsin.

In the most preferred practice and as a useful example, a quantity of alpha-chymotrypsin is initially prepared in a dilution of 1:10,000, corresponding to a ratio of amounts of 1 milligram of alpha-chymotrypsin to 10 milliliters of the solution medium. The volume of the solution is then divided into equal portions of 1 ml, each portion thereby having a concentration of 1/10 mg alpha-chymotrypsin to 1 ml solution medium. The 1 ml portions are then freeze-dried in individual vials. Prior to usage, cellugel, methylcellose, or other such physiologically suitable viscoelastic substances are added thereto. The viscoelastic substance serves to maintain the concentration of the alpha-chymotrypsin to viscoelastic substance, by volume, between approximately 1:15,000 to 1:20,000 in the final dispersion regardless of the quantity of liquid present in the eye, or liquid forming or collecting in the capsule, during the posterior capsule cleaning operation.

DESCRIPTION OF THE PREFERRED EMBODIMENTS

The present invention solves the aforementioned problem of thickening of the capsule because of very fine particles which cannot be seen microscopically during the operation and which form a thickened film on the posterior capsule.

It has surprisingly been discovered that effective cleaning of the posterior capsule in accordance with a first embodiment of the invention can be achieved with the use of a solution of alpha-chymotrypsin in a physiological solvent medium, especially of a physiological saline solution or a glutathion-bicarbonate solution according to Edelhauser, in a dilution of 1:10,000 to 1:30,000, corresponding to an amount ratio of 1 milligram of alpha-chymotrypsin to 10 to 30 milliliters, of the solvent. By treatment of the posterior capsule with such a solution, it is possible to clean the capsule and cellular components that are gathered on the capsule which can thicken to form a film. Treatment of the posterior capsule with such a solution serves also to hinder or prevent the new formation of such thickening.

Trials conducted on donor eyes in which the corneas have been used for complete cornea transplant have shown that with a solution of alpha-chymotrypsin with the above-mentioned dilution of 1:10,000 to 1:30,000, the fibers that hold the posterior capsule are not dissolved, but, rather, that exclusively the remaining components on the capsule are removed.

The preparation can be used in the above-indicated dilution for any extracapsular cataract extraction with or without lens implantation, for cleaning of the posterior capsule. A corresponding diluted solution of the preparation can be produced from commercially available substances which are furnished in the dry form.

Those skilled in the art will appreciate, from what has been said above, that the invention in its broadest aspect relates to the use of alpha-chymotrypsin in a physiologically suitable medium, with the active ingredient, the alpha-chymotrypsin, being present in a concentration effective to clean the posterior lens capsule left behind in the extracapsular cataract operation without dissolving the zonule fibers which hold the lens in tension.

It is conceivable that solutions somewhat more highly concentrated in respect to alpha-chymotrypsin may also be used in order to perform posterior capsule cleaning in compliance with the general guidelines of the present invention. The concentration which is used must, however, be suitably related to the treatment time, as is hereinafter more specifically explained. When performing the extracapsular operation, the first step is to remove the anterior capsule, the darkened lens and the sub or intracapsular posterior rind coating (cortex). After the cavity is filled with air, 0.1 to 0.5 milliliters of the solution according to the present invention are deposited on the inner surface of the posterior capsule by means of a cannule. After the necessary treatment time, the solution is drawn off, and the cavity is washed out. The treatment time is dependent upon the dilution of the solution employed, and it is chosen at about 4½ minutes for a dilution of 1:17000, for example. Solutions having a dilution of more than 1:30,000 need treatment times that would extend the operation needlessly. The use of solutions having a dilution of less than 1:10,000 is undesirable since, on the one hand, they require treatment times that cannot be controlled with the necessary degree of safety, and, on the other hand, the danger that the zonule fibers may be more or less dissolved becomes too great. The optimal range which is to be used in practice is a dilution of approximately 1:15,000 to 1:20,000, with a treatment time between 2 and 3 minutes. The broadest range is from 1: over 10,000 to 1:30,000.

It is possible to add the diluted solution by use of a spongy material that is soaked with 0.1 to 0.5 milliliters of the solution, brought into the cavity where it is in contact with the posterior capsule, and then removed after the required treatment time.

In accordance with the best mode now known to the inventor for practicing a first embodiment of the present invention, there is practiced an improvement in the procedure as described above in the composition contains an effective portion an additional agent or ingredient which is used in order to overcome or combat unwanted further dilution of the alpha-chymotrypsin by liquid which is present in the eye or which may collect in the capsule or be formed in the capsule.

The above-mentioned additional agent or ingredient is, in general, in the nature of a viscoelastic liquid substance which is suited or adapted for intraocular or intraorbital surgical use. Such substances are well known to those skilled in the art. They include, inter alia, methylcellulose, Cellugel ®, and a medical preparation which contains hyaluronic acid and/or the sodium salt thereof and is sold under the trademark "Healon". In addition to other similar substances, there is also a similar preparation which is sold under the trademark "Viscoat".

The very important effects of combining the diluted alpha-chymotrypsin with an agent or ingredient as indicated above include:

(1) avoiding further dilution of the alpha-chymotrypsin by liquid which may be present in the eye, (2) limiting the application area of the alpha-chymotrypsin substance exactly to the desired area of the capsule to be treated, and (3) ensuring a more nearly uniform distribution of the alpha-chymotrypsin over the surface upon which it acts.

The added viscoelastic agent or ingredient is employed to an extent that the ratio of the agent to the alpha-chymotrypsin is, by volume, at least 1:1, whereby the viscoelastic serves to effectively maintain the concentration of alpha-chymotrypsin in the solution at a concentration range of generally 1:10,000 to 1:30,000.

An illustrative, but not limitative, procedure for the preparation of an alpha-chymotrypsin composition of a second and most preferred embodiment of the present invention is as follows. A 1 mg quantity of pure, crystalline, dialyzed and stabilized alpha-chymotrypsin having an enzymatic activity of 5 micro Katal (90IE or 275 U.S.P. units) is diluted in 10 ml of a physiological solution medium, a physiological saline solution, to thereby produce a dilution of 1:10,000. The solution is preferably then divided into 10 equal portions each containing the concentration of 1/10 mg alpha-chymotrypsin in 1 ml of solution medium. The portions are then freeze-dried in vials and sealed. In such a condition, the freeze-dried solution may be stored indefinitely at the proper concentration and in quantities which, when dispersed and suspended in a premeasured physiologically suitable viscoelastic medium, represent accurately meted and conveniently manageable "individual application" quantities of posterior lens cleansing composition. In other words, the quantity of material contained in each vial, when suspended in the viscoelastic medium, is conservatively sufficient, without being unduly wasteful, for a single posterior lens cleaning treatment.

It is conceivable that the solution may be freeze-dried without first being divided into smaller "individual application" quantities. This is not preferred practice, however, since, prior to being mixed with the viscoelastic medium, a small and precise quantity of the freeze-dried matter must first be extracted from the total volume of freeze-dried matter. Such an exact and small quantity of dried material cannot always be extracted and measured with the degree of accuracy required for such delicate eye treatment applications. Consequently, such inaccurately measured quantities may produce compositions which, when prepared, are either too strong or too weak to safely or efficiently (as the case may be) perform effective cleansing of the posterior capsule.

Continuing, but in particular reference to the preferred condition wherein the freeze-dried matter is divided into individual portions, at such time when it is desired to suspend the freeze-dried matter in the viscoelastic medium for use as a posterior capsule cleaning composition, at least one of the vials is opened and the freeze-dried matter contained therein is brought to a final application concentration via the addition of a controlled quantity of the viscoelastic agent. In keeping with the preferred illustrative procedure described supra, the flakes or granules forming the freeze-dried 1/10 mg quantity of alpha-chymotrypsin solution, which was initially at a dilution of 10,000, are brought to a colloidal-like dispersion or suspension in the viscoelastic medium by introducing 1.5 ml (1.5 cc) of the viscoelastic agent into a vial, at the exclusion of air, along with a rough-surfaced mixing ball, then closing the vial and, finally, agitating the vial until the alpha-chymotrypsin is suitably dispersed. The mixing ball may be glass, metal, plastic, or the like. Measurements of the enzymatic activity of the alpha-chymotrypsin/viscoelastic medium dispersion indicate that the viscoelastic agent serves to positively maintain the concentration of the suspended alpha-chymotrypsin in a preferred range of around 1:15,000 to 1:20,000 throughout the posterior capsule cleaning operation. It will be understood, however that any quantity of viscoelastic agent suitable for maintaining the concentration of the suspended alpha-chymotrypsin in the range of 1:greater than 10,000 to 1:30,000 is within the scope of the present invention.

It is believed that a relative reduction in the enzymatic activity of the suspended concentrations of alpha-chymotrypsin (i.e., enzymatic activity corresponding to concentrations generally greater than 1:15,000) in the final application composition as compared to the initial solution concentration of 1:10,000 may be attributed not only to the dispersion concentration ratio but also to the effects of initial dilution and/or freeze-drying on the degree of enzymatic activity of the alpha-chymotrypsin. Moreover, it is further contemplated that, if desired, the composition of the present invention in its final application concentration may be suitably used as an irrigating medium.

While the present invention has been described in connection wit the preferred embodiments, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

I claims as my invention:

1. A method of performing an extracapsular operation for treatment of grey cataract comprising treating a posterior side of the capsule of the lens with a composition of matter consisting essentially of alpha-chymotrypsin in an physiologically suitable medium, the concentration of said alpha-chymotrypsin in the composition being effective to clean the posterior lens capsule left behind in said extracapsular cataract operation and without dissolving the zonule fibers which hold said lens in tension, said composition containing an amount of a physiologically suitable substance effective for combatting further unwanted dilution of the alpha-chymotrypsin during treating the posterior side of the capsule of the lens.

2. The method according to claim 1 wherein said composition has one part alpha-chymotrypsin diluted with greater than 10,000 parts but not more than 30,000 parts physiologically suitable medium.

3. The method according to claim 1 wherein said physiological suitable substance is selected from the group consisting of methylcellulose, a medical preparation containing hyaluronic acid, and a medical preparation containing the sodium salt of hyaluronic acid.

4. The method according to claim 1 wherein said physiologically suitable medium comprises a solvent medium in the form of a solution of aqueous sodium chloride.

5. The method according to claim 1 wherein said physiologically suitable medium comprises a solvent medium in the form of a suitable solution of glutathionbicarbonate according to Edelhauser.

6. The method according to claim 1 wherein said physiologically suitable substance consists of a said viscoelastic substance.

7. The method according to claim 6 wherein said viscoelastic substance is selected from the group consisting of methylcellulose, a medical preparation containing hyaluronic acid, and a medical preparation containing the sodium salt of hyaluronic acid.

8. The method according to claim 2 wherein said physiologically suitable medium consists of a viscoelastic substance.

9. The method according to claim 8 wherein said viscoelastic substance is selected from the group consisting of methylcellulose, a medical preparation containing hyaluronic acid, and a medical preparation containing the sodium salt of hyaluronic acid.

10. The method according to claim 9 wherein said composition has one part alpha-chymotrypsin diluted with from 15,000 to 20,000 parts viscoelastic substance.

11. A method of preparing a composition of matter for treating a posterior side of the capsule of the lens in an extracapsular operation for treatment of grey cataract, said method comprising the steps of:
mixing alpha-chymotrypsin in physiologically suitable solvent medium to form a solution;
dividing the solution into a plurality of substantially equal portions;
freeze-drying said portions;
adding a viscoelastic substance to one of said freeze-dried portions to combat unwanted dilution of alpha-chymotrypsin during treatment of the posterior lens capsule; and
agitating said viscoelastic substance and one of said freeze dried portions to disperse and suspend the material of the freeze dried portion in said viscoelastic substance.

12. A method of preparing a composition of matter for treating a posterior side of the capsule of the lens in an extracapsular operation for treatment of grey cataract, said method comprising the steps of:
mixing a quantity of alpha-chymotrypsin in a quantity of physiologically suitable solvent medium in order to form a solution, said alpha-chymotrypsin being present in said solution in a dilution effective to clean the posterior lens capsule left behind in said extracapsular cataract operation without dissolving the zonule fibers which hold the lens in tension;

adding an effecting quantity of physiologically suitable substance to said solution for combatting unwanted dilution of the alpha-chymotrypsin during treatment of the posterior lens capsule.

13. The method according to claim 12 wherein said composition has one part alpha-chymotrypsin diluted with greater than 10,000 parts but not more than 30,000 parts solvent medium.

14. The method according to claim 13 wherein said composition contains a ratio of physiologically suitable substance to alpha-chymotrypsin of at least 1:1, by volume.

15. The method according to claim 14 wherein said physiologically suitable substance is viscoelastic and selected from the group consisting of methylcellulose, a medical preparation containing the sodium salt of hyaluronic acid.

16. The method according to claim 12 wherein said solvent medium is a physiologically suitable solution of aqueous sodium chloride.

17. The method according to claim 12 wherein said solvent medium is a physiologically suitable solution of glutathion-bicarbonate according to Edelhauser.

18. A composition of matter for treating a posterior side of the capsule of the lens in an extracapsular operation for treatment of grey cataract, said composition consisting essentially of alpha-chymotrypsin in a physiologically suitable medium, said alpha-chymotrypsin being present in a concentration effective to clean the posterior lens capsule left behind in said extracapsular cataract operation without dissolving the zonule fibers which hold said lens in tension, said composition further containing an amount of a viscoelastic substance effective for combatting further unwanted dilution of the alpha-chymotrypsin during treatment of the posterior lens capsule.

19. The composition of matter according to claim 18 wherein said composition has one part alpha-chymotrypsin diluted with greater than 10,000 parts but not more than 30,000 parts physiologically suitable medium.

20. The composition of matter according to claim 19 wherein said composition contains a ratio of viscoelastic substance to alpha-chymotrypsin of at least 1:1, by volume.

21. The composition of matter according to claim 20 wherein said viscoelastic substance i selected from the group consisting of methylcellulose, a medical preparation containing hyaluronic acid, and a medical preparation containing the sodium salt of hyaluronic acid.

22. The composition of matter according to claim 18, wherein said physiologically suitable medium comprises a solvent medium in the form of a solution of aqueous sodium chloride.

23. The composition of matter according to claim 18 wherein said physiologically suitable medium comprises a solvent medium in the form of a solution of glutathion-bicarbonate according to Edelhauser.

24. The composition of matter according to claim 18 wherein said physiologically suitable medium consists of said viscoelastic substance.

25. The composition of matter according to claim 24 wherein said viscoelastic substance is selected from the group consisting of methylcellulose, a medical preparation containing hyaluronic acid, and a medical preparation containing the sodium salt of hyaluronic acid.

26. The composition of matter according to claim 19 wherein aid physiologically suitable medium consists of said viscoelastic substance.

27. The composition of matter according to claim 26 wherein said viscoelastic substance is selected from the group consisting of methylcellulose, a medical preparation containing hyaluronic acid, and a medical preparation containing the sodium salt of hyaluronic acid.

28. The composition of matter according to claim 27 wherein said composition has one part alpha-chymotrypsin diluted with from 15,000 to 20,000 parts viscoelastic substance.

29. A method of preparing a composition of matter for treating a capsule of lens in an extracapsular operation, said method comprising the steps of:
mixing a quantity of alpha-chymotrypsin in a quantity of physiologically suitable solvent medium to form a solution;
dividing the solution to form a plurality of diluted alpha-chymotrypsin portions each containing a sufficient amount of alpha-chymotrypsin for treating a posterior side of the capsule of the lens in an extracapsular operation for treatment of grey cataract;
freeze-drying each diluting alpha-chymotrypsin portion; and
combining at least one of the freezed dried alpha-chymotrypsin portions with a physiologically suitable substance for combating unwanted dilution of the alpha-chymotrypsin during treatment of the posterior capsule lens.

30. The method according to claim 29 wherein the freezed dried alpha-chymotrypsin portion in the physiologically suitable substance is present in the ratio of between 1:10,000 and 1:30,000.

31. The method according to claim 29 wherein the freezed dried alpha-chymotrypsin portion in the physiologically suitable substance is present in the ratio of 1:17,000.

* * * * *